US009517199B2

(12) United States Patent
de la Fuente et al.

(10) Patent No.: US 9,517,199 B2
(45) Date of Patent: *Dec. 13, 2016

(54) TREATMENT FOR CHRONIC MYOCARDIAL INFARCT

(71) Applicant: BioCardia, Inc., San Carlos, CA (US)

(72) Inventors: Luis M. de la Fuente, Buenos Aires (AR); Simon H. Stertzer, Santa Fe, NM (US); Julio Argentieri, Buenos Aires (AR); Eduardo Penaloza, Buenos Aires (BR); Peter A. Altman, Menlo Park, CA (US)

(73) Assignee: BioCardia, Inc., San Carlos, CA (US)

( * ) Notice: Subject to any disclaimer, the term of this patent is extended or adjusted under 35 U.S.C. 154(b) by 73 days.

This patent is subject to a terminal disclaimer.

(21) Appl. No.: 14/630,305

(22) Filed: Feb. 24, 2015

(65) Prior Publication Data

US 2015/0164786 A1 Jun. 18, 2015

Related U.S. Application Data

(63) Continuation of application No. 13/953,961, filed on Jul. 30, 2013, which is a continuation of application No. 11/735,869, filed on Apr. 16, 2007, now Pat. No. 8,496,926.

(51) Int. Cl.
| | |
|---|---|
| *A01N 63/00* | (2006.01) |
| *A61K 9/00* | (2006.01) |
| *A61K 35/28* | (2015.01) |
| *A61K 35/14* | (2015.01) |
| *A61K 35/32* | (2015.01) |
| *A61K 35/35* | (2015.01) |

(52) U.S. Cl.
CPC ............. *A61K 9/0019* (2013.01); *A61K 35/14* (2013.01); *A61K 35/28* (2013.01); *A61K 35/32* (2013.01); *A61K 35/35* (2013.01)

(58) Field of Classification Search
None
See application file for complete search history.

(56) References Cited

U.S. PATENT DOCUMENTS

| | | |
|---|---|---|
| 6,585,716 B2 | 7/2003 | Altman |
| 6,878,371 B2 | 4/2005 | Ueno et al. |
| 7,658,915 B2 | 2/2010 | Freyman |
| 7,799,349 B2 | 9/2010 | Ueno et al. |
| 8,496,926 B2 | 7/2013 | De La Fuente et al. |
| 2002/0037278 A1 | 3/2002 | Ueno et al. |
| 2004/0131585 A1 | 7/2004 | Itescu |
| 2004/0161421 A1 | 8/2004 | Kornowski et al. |
| 2009/0148415 A1 | 6/2009 | De La Fuente et al. |
| 2013/0323212 A1 | 12/2013 | De La Fuente et al. |

FOREIGN PATENT DOCUMENTS

EP 1171165 B1 5/2007

OTHER PUBLICATIONS

Office action dated Aug. 10, 2015 for U.S. Appl. No. 13/953,961.
De La Fuente, et al. Transendocardial autologous bone marrow in chronic myocardial infarction using a helical needle catheter: 1-year follow-up in an open-label, nonrandomized, single-center pilot study (The TABMMI Study), 154 American Heart Journal 79 (Jul. 2007).
Dohmann, et al. Transendocardial autologous bone marrow mononuclear cell injection in ischemi heart failure, 112 Circulation 521, Jul. 26, 2005.
Fuchs, et al. Catheter-based autologous bone marrow myocardial injection in no-option patients with advanced coronary artery disease, 41 JACC 1721 May 21, 2003.
Galinanes, et al. Autotransplantation of unmanipulated bone marrow into scarred myocardium is safe and enhances cardiac function in humans. Cell Transplant. 2004;13(1):7-13.
Itescu, et al. Reparative effects of allogeneic mesenchymal precursor cells delivered transendocardially in experimental nonischemic cardiomyopathy, 3 JACC Interventions 974 (2010).
Losordo, et al. Intramyocardial transplantation of autologous CD34 stem cells for intractable angina, 115 Circulatin 3165 (Jun. 2007).
Losordo, et al. Phase 1/2 placebo-controlled, double-blind, dose-escalating, trial of myocardial vascular endothelial growth factor 2 gene transfer by catheter delivery in patients with chronic myocardial ischemia, 10 circulation 2012, 2013 (2002).
Marat, et al. Revascularization in ischemic heart with autologous bone marrow transplantation, 26 Japan Journal of Cardiovascular Surgery 248 (1997).
Notice of allowance dated Mar. 26, 2013for U.S. Appl. No. 11/735,869.
Office action dated Jan. 3, 2013 for U.S. Appl. No. 11/735,869.
Office action dated Jan. 30, 2012 for U.S. Appl. No. 11/735,869.
Office action dated Mar. 17, 2011 for U.S. Appl. No. 11/735,869.
Office action dated Apr. 18, 2012 for U.S. Appl. No. 11/735,869.
Office action dated Jun. 17, 2010 for U.S. Appl. No. 11/735,869.
Perin, et al. Transendocardial, autologous bone marrow cell transplantation for severe chronic ischemic heart failure, 107 Circulation 2294, May 13, 2003.
Pittenger, et al. 1999. Multilineage potential of adult human mesenchymal stem cells. Science 284: 143-147.
Seth, et al. Percutaneous intracoronary cellular cardiomyoplasty for nonischemic cardiomyopathy, 48 JACC 2350 (Dec. 5, 2006).
Shake, et al. Mesenchymal stem cell implantation in a swine myocardial infarct model: engraftment and functional effects. Ann Thorac Surg 73: 1919-1926.
Strauer, et al. Renegeration of human infarcted heart muscle by intracoronary autologous bone marrow cell transplantation in chronic coronary artery disease. J Am Coll Cariol 46: 1651-58.
Tse, et al. Angiogenesis in ischaemic myocardium by intramyocardial autologous bone marrow mononuclear cell implantation, 361 Lancet 47, Jan. 4, 2003.
U.S. Appl. No. 13/953,961 Notice of Allowance dated Aug. 3, 2016.

*Primary Examiner* — Lora E Barnhart Driscoll
(74) *Attorney, Agent, or Firm* — Wilson Sonsini Goodrich & Rosati

(57) ABSTRACT

A method of treating chronic post-myocardial infarction including helical needle transendocardial delivery of autologous bone marrow (ABM) mononuclear cells around regions of hypo or akinesia in chronic post-myocardial infarction (MI) patients. The treatment is safe and improves ejection fraction (EF).

40 Claims, 3 Drawing Sheets

TREATMENT FOR CHRONIC MYOCARDIAL INFARCT

CROSS-REFERENCE TO RELATED APPLICATIONS

This application is a continuation of U.S. patent application Ser. No. 13/953,961, filed Jul. 30, 2013, which is a continuation of U.S. patent application Ser. No. 11/735,869, filed Apr. 16, 2007, now U.S. Pat. No. 8,496,926, the entire contents of which are incorporated herein by reference in their entirety.

BACKGROUND OF THE INVENTION

Field of the Invention

The inventions described below relate the field of cardiology.

Chronic Myocardial Infarction refers to myocardial tissue which has died as the result of myocardial infarct, and has over the course of time become remodeled to scar tissue within the myocardium. Left untreated, myocardial infarction induces global changes in the ventricular architecture in a process called ventricular remodeling. Eventually, the patient experiences ventricular dilation and ventricular dysfunction. This ventricular remodeling is a major cause of heart failure.

While there are several suggested means of ameliorating the effects of acute myocardial infarction (immediately after the event leading to infarct), no significant therapy has been proposed or implemented for the amelioration or reversal of chronic myocardial infarction and the deleterious effects of infracted tissue after substantial transformation or remodeling of the infracted tissue to scar tissue.

SUMMARY OF THE INVENTION

The method of treating chronic myocardial infarction described below comprises injection of autologous bone marrow derived mononuclear cells, or cells derived from those mononuclear cells, into the myocardium. These cells are injected near or in the chronic infracted tissue.

DETAILED DESCRIPTION OF THE INVENTION

Figure 1:
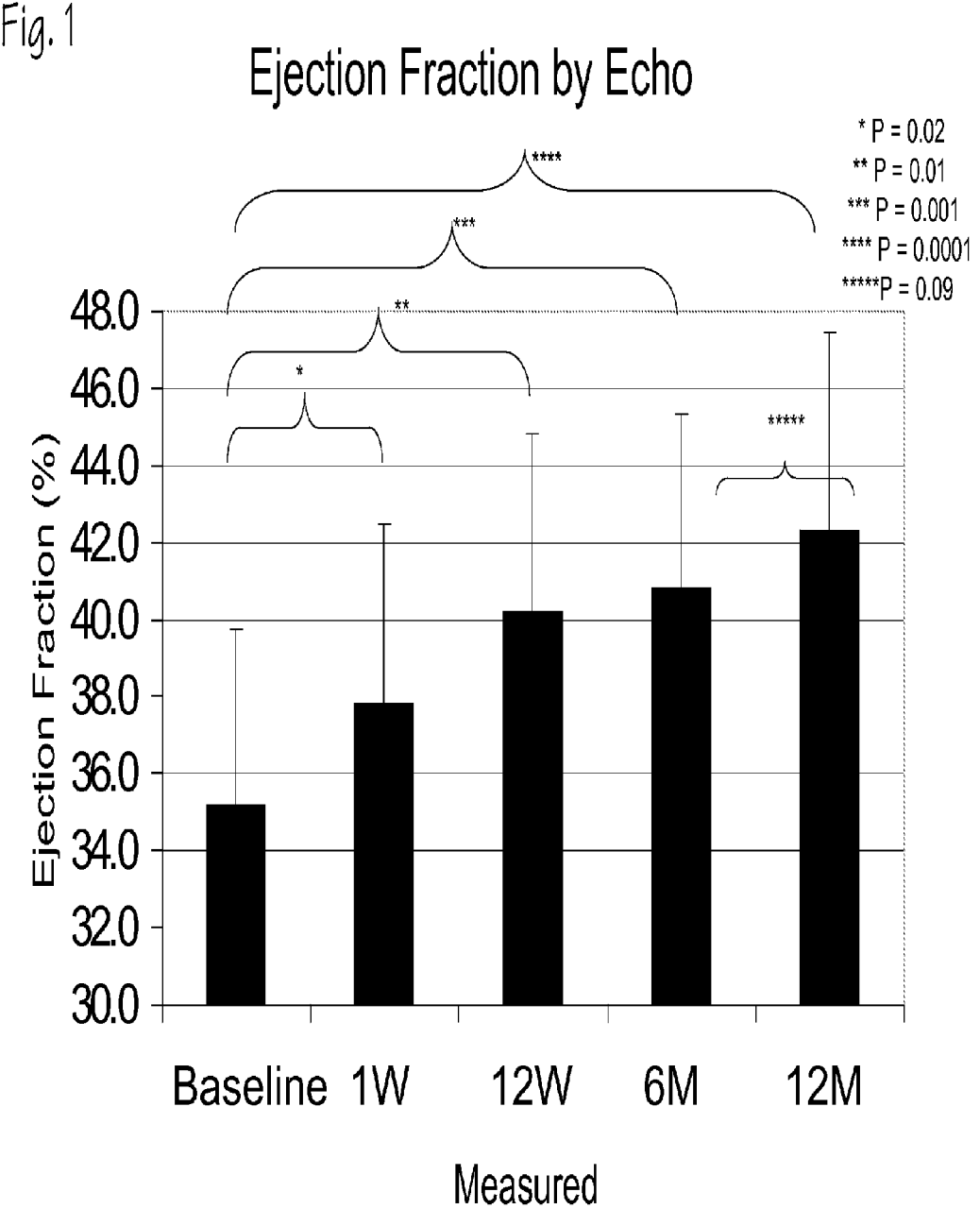
FIG. 1 is a graph showing improvement in ejection fraction of the patients in an experimental group, after injection of autologous bone marrow derived mononuclear cells.

Chronic myocardial infarction refers to the condition of infracted tissues after the infracted tissue has been remodeled by natural wound healing responses and comprises, after such remodeling, scar tissue, which is substantially dead. This is distinct from ischemic tissue characteristic of chronic ischemia, which refers to tissue which is chronically hypoxic due to lack of sufficient blood flow, but is still viable even if not fully active in the muscular and electro-physiologically activity of the heart. The method starts with identifying patients afflicted with chronic myocardial infarction. Once patients with chronic myocardial infarction are identified, their suitability for treatment under the method currently requires a low ejection fraction (less that about 40%). In our experiments aimed at determining if the treatment is safe, we included patients with left ventricular dysfunction (less that about 40% but not less than about 30%) that were not candidates for ventricular aneurysm surgery, implantable defibrillators, or valve repair or replacement, while excluding patients with active infections, malignancies, high grade atrioventricular block, sustained ventricular tachyarrythmias, a recent MI (less than 4 weeks old), presence of an artificial aortic valve, recent history of alcohol or drug abuse or evidence of other multi-system disease. However, given the results of our experiments, we expect that the treatment could benefit all patients suffering from chronic myocardial infarction so long as they can tolerate the procedure.

Immediately prior to the catheterization necessary to delivery the autologous bone marrow cells, the cells are collected from suitable sites within the patient, such as the posterior iliac crest, vertebral body and/or sternum. Bone marrow mononuclear cells are isolated by suitable methods such as density gradient on Ficoll-Paque Plus tubes (GE Healthcare, UK) through 100 .mu.m nylon mesh to remove cell aggregates, and re-suspended in Ringers solution at a concentration of $1.times.10.sup.8$ cells/ml in a total volume of 1.3 ml. These cells are prepared for injection back into the patient within about 4 to 6 hours after harvesting. The bone marrow derived mononuclear cells include CD-34 positive cells, CD-133 positive cells, and CD-90 positive cells (mesenchymal stem cells) which may also be separately isolated for injection to treat chronic myocardial infarction. Preferably at least 40% of the cells isolated comprise CD-34 positive cells, CD-90 positive cells, and CD-133 positive cells or a combination thereof.

Just prior to cell delivery, the doctors performing the cell delivery use various techniques, including ECG's, echocardiography, and baseline orthogonal ventriculography data to define the target infarct tissue zones. Access to the target infarct zone is preferably via catheter, transendocardially (with the catheter tip in the endocardial space) into the myocardium. Intramyocardial delivery may also be accomplished through a trans-coronary venous approach as described in BioCardia's U.S. Pat. No. 6,585,716, through a trans-coronary arterial approach, or a trans-epicardial approach. Any suitable catheter system can be used, though the BioCardia™ helical infusion catheter and steerable guide catheter are particularly well suited to the method. Dosage may range from three injections of 0.1 to 0.2 ml of cell solution at a concentration of $10.sup.8$ (one hundred million) cells/ml (totaling about $5.times.10.sup.7$ cells) to 11 injections of 0.1 to 0.2 ml of cell solution at a concentration of $1.2.times.10.sup.8$ cells/ml for a total of $1.2.times.10.sup.8$ cells spread over numerous injection cites proximate the target infarct tissue. The solution containing the cells is injected near or at the site of an infarct, in several small injections proximate the target infarct. Each injection is performed slowly, and the helical injection catheter is left in the injection site to dwell for a substantial period (about 15 to 30 seconds) to prevent back-leakage of the solution into the endocardial space of the ventricle.

Figure 2:
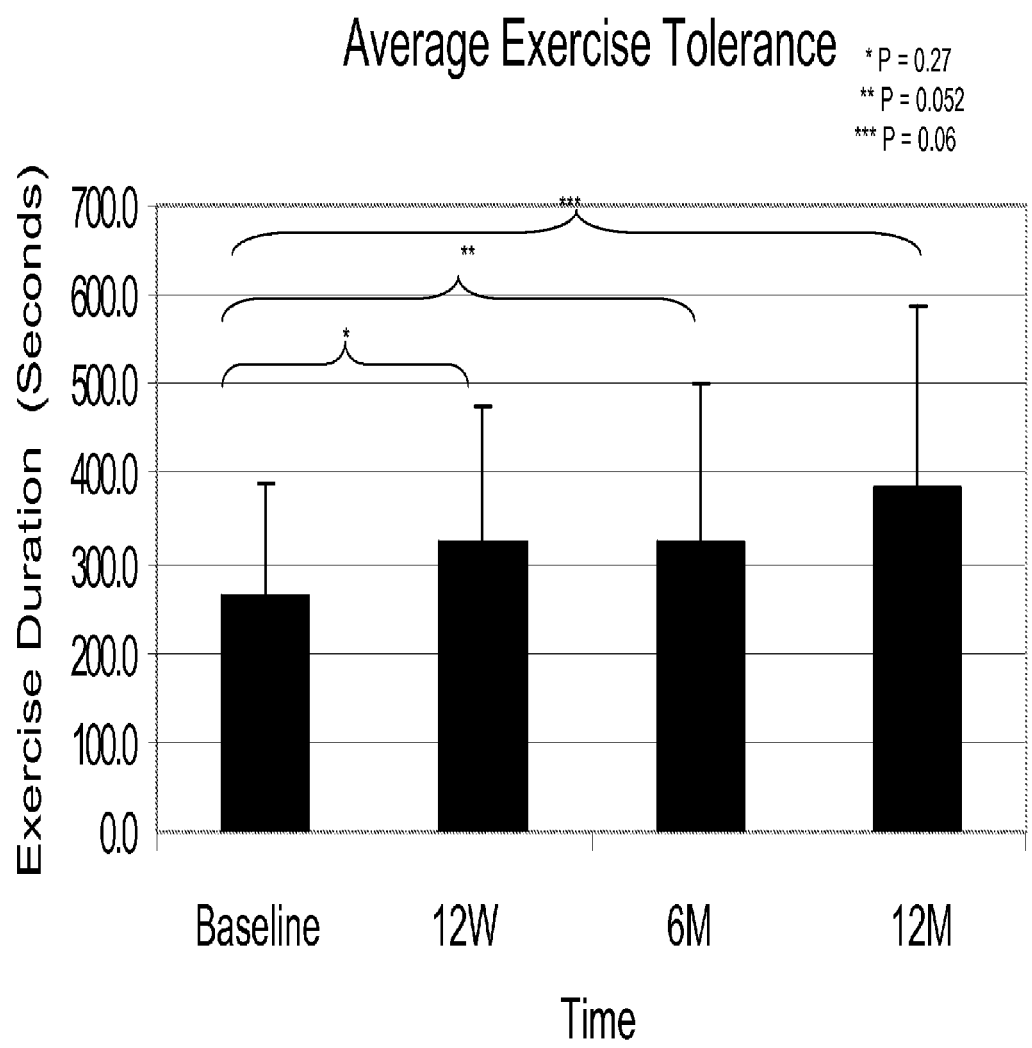
FIG. 2 is a graph showing improvement in exercise tolerance of the patients in an experimental group, after injection of autologous bone marrow derived mononuclear cells.
Figure 3:
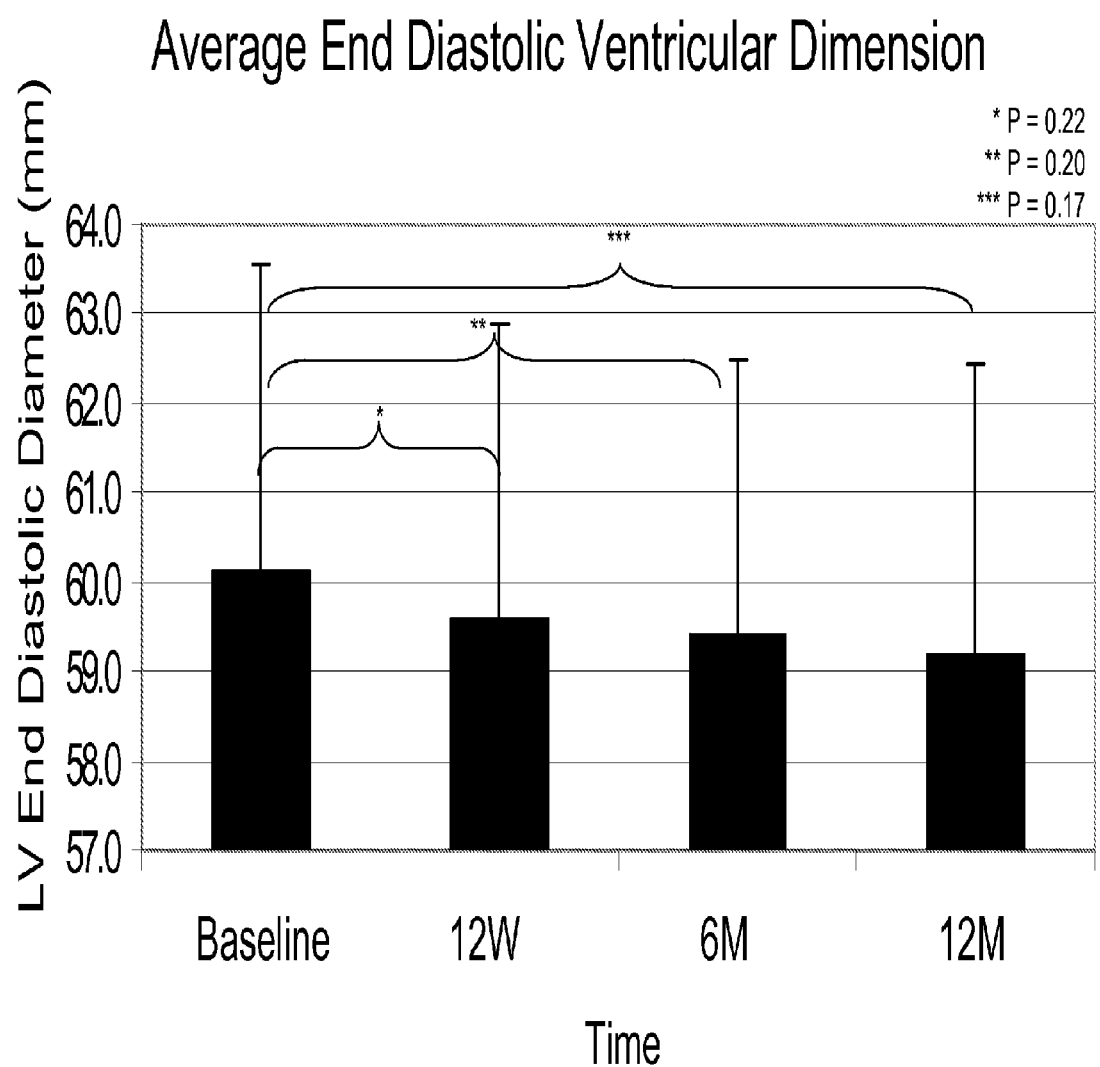
FIG. 3 is a graph showing improvement in ventricular diastolic volume of the patients in an experimental group, after injection of autologous bone marrow derived mononuclear cells.

The efficacy of the treatment is reflected in FIGS. 1 through 3, which show that chronic myocardial infarct patients treated with autologous bone marrow derived mononuclear cells benefit from improved ejection fraction, improved exercise tolerance, and reduced ventricular dilation. As shown in FIG. 1, ejection fraction of the patients, as measured by 2D echocardiography, demonstrates a statistically significant increase at 1 week (P=0.02), 12 weeks (P=0.01), 6 months (P=0.001), and 12 months (P=0.0001) as compared to baseline. All patients in the experimental group showed an increase in this parameter over baseline at 6 months and 12 months. Smaller long term improvements in diastolic volume and exercise tolerances were noted in our experimental group, as shown in FIGS. 2 and 3. Given the results of our experiment with a small number of patients, the method results in significantly improved ejections fraction, reduced ventricular dilation, and improved exercise tolerance. No increase in ventricular arrhythmias was detected in any patient in the experimental group.

Peripheral blood derived mononuclear cells (PBMC) and adipose tissue derived mononuclear cells can be also be used in the treatment, as can cells derived from those mononuclear cells harvested from the peripheral blood or adipose tissue. While the preferred embodiments of the devices and methods have been described in reference to the environment in which they were developed, they are merely illustrative of the principles of the inventions. Other embodiments of the method, including sources of cells and methods of isolation, and particular constituent cells of the injected cell population may be devised without departing from the spirit of the inventions and the scope of the appended claims.

What is claimed is:

1. A method of treating chronic myocardial infarction comprising:
   identifying a patient with chronic myocardial infarction with areas of chronic myocardial infarct within the patient's myocardium; and
   transendocardially injecting a therapeutic preparation comprising 30,000,000 to 264,000,000 concentrated mononuclear cells into myocardium of the patient near or in an area of chronic infarcted tissue resulting from chronic myocardial infarct, where said mononuclear cells were harvested from autologous bone marrow cells from the patient.

2. The method of claim 1, wherein said at least 40% of said concentrated mononuclear cells are
   (a) CD-34 positive cells,
   (b) CD-90 positive cells,
   (c) CD-133 positive cells, or
   (d) a combination of CD-34 positive cells, CD-90 positive cells, and/or CD-133 positive cells.

3. The method of claim 1 wherein said concentrated mononuclear cells comprises at least 40% CD-34 positive cells.

4. The method of claim 1 wherein said concentrated mononuclear cells comprises at least 40% CD-133 positive cells.

5. A method of treating chronic myocardial infarction comprising:
   identifying a patient with chronic myocardial infarction with areas of chronic myocardial infarct within the patient's myocardium;
   transendocardially injecting a therapeutic preparation into the myocardium of the patient near or in areas of chronic myocardial infarct, where said therapeutic preparation comprises concentrated CD-34 positive cells and CD-133 positive cells harvested from autologous bone marrow cells of the patient and suspended in solution.

6. The method of claim 4, wherein said at least 40% of said concentrated mononuclear cells are
   (a) CD-34 positive cells,
   (b) CD-90 positive cells,
   (c) CD-133 positive cells, or
   (d) a combination of CD-34 positive cells, CD-90 positive cells, and/or CD-133 positive cells.

7. The method of claim 5 wherein said therapeutic preparation comprising at least 40% CD-34 positive cells.

8. The method of claim 5 wherein said therapeutic preparation of the cells comprising at least 40% CD-133 positive cells.

9. The method of claim 5 wherein a concentration of mononuclear cells including CD-34 positive cells, CD-133 positive cells or a combination thereof is in the range from $10^8$ concentrated cells/ml of solution to $1.2 \times 10^8$ concentrated cells/ml of solution.

10. A method of treating chronic myocardial infarction comprising:
    identifying a patient with chronic myocardial infarction having an ejection fraction less than 40%; and
    transendocardially injecting a therapeutic preparation comprising concentrated CD-34 positive and CD-133 positive mononuclear cells into myocardium of the patient, where said mononuclear cells were harvested from autologous bone marrow cells from the patient.

11. The method of claim 10 wherein the therapeutic preparation comprises 30,000,000 to 264,000,000 concentrated mononuclear cells comprising CD-34 positive and CD-133 positive mononuclear cells.

12. The method of claim 10, wherein said at least 40% of said concentrated mononuclear cells are
    (a) CD-34 positive cells,
    (b) CD-90 positive cells,
    (c) CD-133 positive cells, or
    (d) a combination of CD-34 positive cells, CD-90 positive cells, and/or CD-133 positive cells.

13. The method of claim 10 wherein said therapeutic preparation comprises at least 40% CD-34 positive cells.

14. The method of claim 10 wherein said therapeutic preparation comprises at least 40% CD-133 positive cells.

15. A method of treating chronic myocardial infarction comprising:
    identifying a patient with areas of chronic myocardial infarct and/or ischemic tissue within the patient's myocardium 10-13 are directed at treat; and
    transendocardially injecting a therapeutic preparation comprising concentrated CD-34 positive and CD-133 positive mononuclear cells into myocardium of the patient near or in said areas of chronic infarcted tissue and/or ischemic tissue, where said mononuclear cells were harvested from autologous bone marrow cells from the patient and were injected with a helical needle.

16. The method of claim 15 wherein the therapeutic preparation comprises 30,000,000 to 264,000,000 000 concentrated mononuclear cells comprising concentrated CD-34 positive and CD-133 positive mononuclear cells.

17. The method of claim 15, wherein said at least 40% of said concentrated mononuclear cells are
    (a) CD-34 positive cells,
    (b) CD-90 positive cells,
    (c) CD-133 positive cells, or
    (d) a combination of CD-34 positive cells, CD-90 positive cells, and/or CD-133 positive cells.

18. The method of claim 15 wherein said therapeutic preparation comprises at least 40% CD-34 positive cells.

19. The method of claim 15 wherein said therapeutic preparation comprises at least 40% CD-133 positive cells.

20. A method of treating chronic myocardial infarction comprising:
identifying a patient with areas of chronic myocardial infarct and/or ischemic tissue within the patient's myocardium; and
transendocardially injecting a therapeutic preparation comprising concentrated CD-34 positive and CD-133 positive mononuclear cells into myocardium of the patient proximate said areas of chronic infarcted tissue and/or ischemic tissue, where said mononuclear cells were harvested from autologous bone marrow cells from a posterior iliac crest of the patient.

21. The method of claim 20 wherein the therapeutic preparation comprises 30,000,000 to 264,000,000 000 concentrated mononuclear cells comprising concentrated CD-34 positive and CD-133 positive mononuclear cells.

22. The method of claim 20, wherein said at least 40% of said concentrated mononuclear cells are
(a) CD-34 positive cells,
(b) CD-90 positive cells,
(c) CD-133 positive cells, or
(d) a combination of CD-34 positive cells, CD-90 positive cells, and/or CD-133 positive cells.

23. The method of claim 20 wherein said therapeutic preparation comprises at least 40% CD-34 positive cells.

24. The method of claim 20 wherein said therapeutic preparation comprises at least 40% CD-133 positive cells.

25. A method of treating chronic myocardial infarction comprising:
identifying a patient with areas of chronic myocardial infarct and/or ischemic tissue within the patient's myocardium; and
transendocardially injecting a therapeutic preparation comprising concentrated CD-34 positive and CD-133 positive mononuclear cells into myocardium of the patient near or in said areas of chronic infarcted tissue and/or ischemic tissue, where said mononuclear cells were harvested from autologous bone marrow cells, filtered and resuspended.

26. The method of claim 25 wherein the mononuclear cells were filtered through a 100 µm mesh to remove cell aggregations.

27. The method of claim 25 wherein the therapeutic preparation comprises 30,000,000 to 264,000,000 000 concentrated mononuclear cells comprising concentrated CD-34 positive and CD-133 positive mononuclear cells.

28. The method of claim 25, wherein said at least 40% of said concentrated mononuclear cells are
(a) CD-34 positive cells,
(b) CD-90 positive cells,
(c) CD-133 positive cells, or
(d) a combination of CD-34 positive cells, CD-90 positive cells, and/or CD-133 positive cells.

29. The method of claim 25 wherein said therapeutic preparation comprises at least 40% CD-34 positive cells.

30. The method of claim 25 wherein said therapeutic preparation comprises at least 40% CD-133 positive cells.

31. A method of treating chronic myocardial infarction comprising:
identifying a patient with areas of chronic myocardial infarct and/or ischemic tissue within the patient's myocardium; and
transendocardially injecting a therapeutic preparation comprising concentrated CD-34 positive and CD-133 positive mononuclear cells into myocardium of the patient near or in said areas of chronic infarcted tissue and/or ischemic tissue, where said mononuclear cells were harvested from adipose tissue from the patient.

32. The method of claim 31 wherein the therapeutic preparation comprises 30,000,000 to 264,000,000 000 concentrated mononuclear cells comprising concentrated CD-34 positive and CD-133 positive mononuclear cells.

33. The method of claim 31, wherein said at least 40% of said concentrated mononuclear cells are
(a) CD-34 positive cells,
(b) CD-90 positive cells,
(c) CD-133 positive cells, or
(d) a combination of CD-34 positive cells, CD-90 positive cells, and/or CD-133 positive cells.

34. The method of claim 31 wherein said therapeutic preparation comprises at least 40% CD-34 positive cells.

35. The method of claim 31 wherein said therapeutic preparation comprises at least 40% CD-133 positive cells.

36. A method of treating chronic myocardial infarction comprising:
identifying a patient with areas of chronic myocardial infarct and/or ischemic tissue within the patient's myocardium; and
transendocardially injecting a therapeutic preparation comprising concentrated CD-34 positive and CD-133 positive mononuclear cells into myocardium of the patient near or in said areas of chronic infarcted tissue and/or ischemic tissue, where said mononuclear cells were harvested from peripheral blood from the patient.

37. The method of claim 36 wherein the therapeutic preparation comprises 30,000,000 to 264,000,000 000 concentrated mononuclear cells comprising concentrated CD-34 positive and CD-133 positive mononuclear cells.

38. The method of claim 36, wherein said at least 40% of said concentrated mononuclear cells are
(a) CD-34 positive cells,
(b) CD-90 positive cells,
(c) CD-133 positive cells, or
(d) a combination of CD-34 positive cells, CD-90 positive cells, and/or CD-133 positive cells.

39. The method of claim 36 wherein said therapeutic preparation comprises at least 40% CD-34 positive cells.

40. The method of claim 36 wherein said therapeutic preparation comprises at least 40% CD-133 positive cells.

* * * * *